(12) United States Patent
Gilligan

(10) Patent No.: US 7,358,252 B2
(45) Date of Patent: Apr. 15, 2008

(54) 4-(2-BUTYLAMINO)-2,7-DIMETHYL-8-(2-METHYL-6-METHOXYPYRID-3-YL)PYRAZOLO-[1,5-A]-1,3,5-TRIAZINE, ITS ENANTIOMERS AND PHARMACEUTICALLY ACCEPTABLE SALTS AS CORTICOTROPIN RELEASING FACTOR RECEPTOR LIGANDS

(75) Inventor: Paul J. Gilligan, Wilmington, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 11/593,715

(22) Filed: Nov. 7, 2006

(65) Prior Publication Data

US 2007/0054913 A1    Mar. 8, 2007

Related U.S. Application Data

(60) Division of application No. 10/358,652, filed on Feb. 5, 2003, now Pat. No. 7,157,578, which is a continuation of application No. 10/092,312, filed on Mar. 6, 2002, now abandoned.

(60) Provisional application No. 60/275,403, filed on Mar. 13, 2001.

(51) Int. Cl.
*A61K 31/53* (2006.01)
*A61P 25/02* (2006.01)
*A61P 25/04* (2006.01)
*C07D 403/12* (2006.01)

(52) U.S. Cl. .................................. 514/246; 544/212
(58) Field of Classification Search ................ 514/246; 544/212
See application file for complete search history.

(56) References Cited

U.S. PATENT DOCUMENTS

| 6,191,131 B1 | 2/2001 | He et al. |
| 6,194,410 B1 | 2/2001 | Bos et al. |
| 6,218,397 B1 | 4/2001 | Chen |
| 6,642,230 B2 | 11/2003 | Wilde et al. |

FOREIGN PATENT DOCUMENTS

| RU | 2124016 | 12/1998 |
| RU | 97100192 | 2/1999 |
| RU | 99105137 | 1/2001 |
| RU | 2201929 | 4/2003 |
| RU | 2221799 | 1/2004 |
| WO | WO 95/10506 | 4/1995 |
| WO | WO 95/33750 | 12/1995 |
| WO | WO 97/35539 | 10/1997 |
| WO | WO 97/35846 | 10/1997 |
| WO | WO 97/44308 | 11/1997 |
| WO | WO 98/03510 | 1/1998 |
| WO | WO 99/01439 | 1/1999 |
| WO | WO 99/01454 | 1/1999 |
| WO | WO 99/11643 | 3/1999 |
| WO | WO 99/38868 | 8/1999 |
| WO | WO 99/51608 | 10/1999 |
| WO | WO 00/01675 | 1/2000 |

OTHER PUBLICATIONS

He, Liql, et al. 4-(1,3-dimethoxyprop-2-ylamino)-2,7-dimethyl-8-(2,4-dichlorophenyl) pyrazolo [1,5-a]-1,3,5-triazine: A Potent, Orally Bioavailable CRF$_1$ Receptor Antagonist, Journal of Medicinal Chemistry, American Chemical Society, Washington, US., vol. 43, 2000, pp. 449-456, XP002106777, ISSN: 0022-2623.

Wermuth et al.; Molecular Variations Based on Isosteric Replacement; The Practice of Medicinal Chemistry, 1996, pp. 203-237, XP 002190259.

Arato, M., et al.; Elevated CSF CRF in suicide victims; Biol Psychiatry, 1989, 25, pp. 355-359.

Banki, C.M., et al.; CSF corticotrophin-releasing factor-like immunoreactivity in depression and schizophrenia; Am. J. Psychiatry, Jul. 1987, pp. 873-877.

Berridge, C.W., et al.; A corticotropin-releasing factor antagonist reverses the stress-induced changes of exploratory behavior in mice; Hormones and Behavior, 1987, 21, pp. 393-401.

Berridge, C.W., et al.; Corticotropin-releasing factor elicts naloxone sensitive stress-like alterations in exploratory behavior in mice; Regulatory Peptides, 1986; 16; pp. 83-93.

Blalock, J.E.; A molecular basis for bidirectional communication between the immune and neuroendoctrine systems; Physiological Reviews, Jan. 1989, 69(1), pp. 1-32.

Britton, K.T., et al.; Chlordiazepoxide attenuates response suppression induced by corticotrophin-releasing factor in the conflict test; Psychopharmacology, 1985, 86; pp. 170-174.

(Continued)

*Primary Examiner*—Venkataraman Balasubram
(74) *Attorney, Agent, or Firm*—Hoffmann & Baron LLP

(57) ABSTRACT

Corticotropin releasing factor (CRF) antagonists of Formula (I):

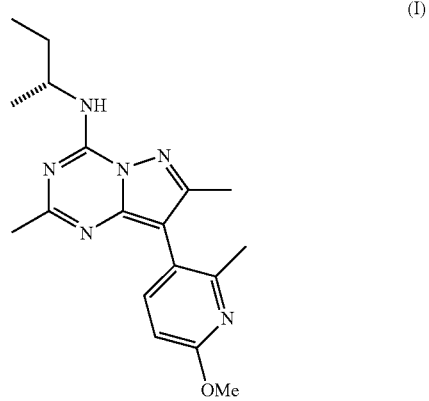

and its use in treating anxiety, depression, and other psychiatric, neurological disorders as well as treatment of immunological, cardiovascular or heart-related diseases and colonic hypersensitivity associated with psychopathological disturbance and stress.

2 Claims, No Drawings

OTHER PUBLICATIONS

Britton, K.T., et al., Corticotropin releasing factor and amphetamine exaggerate partial agonist properties of benzodiazepine antagonist Ro 15-1788; Psychopharmacology, 1988, 94, pp. 306-311.

Britton, D.R., et al.; Intraventricular corticotrophin-releasing factor enhances behavioral effect of novelty; Life Sciences, May 12, 1982, 31(4), pp. 363-367.

Bundgard, H., Advanced Drug Delivery Reviews, 1992, 8, pp. 1-38.

Chrousos, G.P., et al; Int. J. Obesity, 2000, 24 (Supp. 2); S50-S55.

DeSouza, E.B., et al.; Corticotropin-releasing factor receptors are widely distributed within the rat central nervous system: An autoradiographic study; J. Neuroscience, Dec. 1985; 5(12); pp. 3189-3203.

DeSouza, E.B.; CRH defects in Alzheimer's and other neurologic diseases; Hospital Practice, Sep. 15, 1998, pp. 59-71.

Dunn, A.J., et al.; Physiological and behavioral responses to corticotrophin-releasing factor administration: is CRF a mediator of anxiety or stress responses?; Brain Research Reviews, 1990; 15, 71-100.

France, R.D., et al.; CSF corticotrophin-releasing factor-like immunoactivity in chronic pain patients with and without major depression; Biol. Psychiatry, 1988, 23, pp. 86-88.

Gilligan, P.J. et al.; J. Med. Chem.; 2000, 43, pp. 1641-1660.

Gold, P.W. et al.; Psychiatric implications of basic and clinical studies with corticotrophin-releasing factor; Am. J. Psychiatry, May 1984, 141(5), pp. 619-627.

Gold, P.W. et al., New Eng. J. Med., 1986, 314, pp. 1129.

Grigoriadis, D.E., et al.; Effects of chronic antidepressant and benzodiazepine treatment on corticotrophin-releasing-factor receptors in rat brain and pituitart; Neurophychopharmacology, 1989, 2(1); pp. 53-60.

Holtsboer, F., et al.; Acth and multisteroid responses to corticotrophin-releasing factor in depressive illness: Relationship to multisteroid responses after acth stimulation and dexamethasone suppression; Psychoneuroendocrinology, 1984, 9(2), 147-160.

Koob, G.F., Stress corticotrophin-releasing factor, and behavior; Perspectives on Behavioral Medicine, 1985, 2, pp. 39-52.

Koob, G.F., Ann. N.Y. Acad. Sci., 2000, 909, pp. 170-185.

Krogsgaard-Larsen, et al.; Design and applications of prodrugs; A textbook of Drug Design and Development; 1991, Chapter 5, pp. 113-191.

McCarthy et al.; Cuur. Pharm. Res.; 1999, 5, pp. 289-315.

Maillot, C. et al.; Gastroenterology, 2000, 119, pp. 1569-1579.

Morley, J.E. et al.; Minireview-neuropeptides: conductors of the immune orchestra; Life Sciences, 1987, 41, pp. 527-544.

Mastorakos, G., et al.; Ann. N.Y. Acad. Sci.; 2000, 900, pp. 95-106.

Nakeya, N. et al.; Chem. Pharm. Bull.; 1984, 32, pp. 692.

Nemeroff, C.B. et al.; Reduced corticotrophin releasing factor binding sites in the frontal cortex of suicide victims; Arch Gen. Psychiatry, Jun. 1988, 45, pp. 577-579.

Nemeroff, C.B.; Elevated concentrations of CFS corticotrophin-releasing factor-like immunoreactivity in depressed patients; Science; Dec. 14, 1984, 226, pp. 1342-1344.

Nemeroff, C.B., Corticotropin-releasing factor; basic and clinical studies of a neuropeptide; CRC Press, Inc. 1990, pp. 221-224.

Newport, D.J. et al.; Curr.Opin. Neurobiology, 2000, 10, pp. 211-218.

Owens, M.J. et al.; Expert Opin. Invest. Drugs; 1999, 8, pp. 1849-1858.

Remington's Pharmaceutical Sciences, 17$^{th}$ Ed., p. 1419.

Rivier, J. et al.; Characterization of rat hypothalamic corticotrophin-releasing factor; Proc. Nat. Acad. Sci. USA, Aug. 1983, 80, pp. 4851-4855.

Sapolsky, R.M.; Hypercortisolism among socially subordinate wild baboons originates at the CNS level; Arch. Gen. Psychiatry, Nov. 1989, 46, pp. 1047-1051.

Swerdlow, N.R. et al.; Corticotropin-releasing factor poteniates acoustic startle in rats: blockage by chlordiazepoxide; Psychopharmacology, 1986, 88, pp. 147-152.

Webster, E. et al.; Ann. N.Y. Acad. Sci.; 1998, 840, pp. 21-32.

Widder, K. et al.; Ed. Academic Press; 1985; 42, pp. 309-396.

Vale, W. et al.; Characterization of a 41-risidue ovine hypothalamic peptide that stimulates secretion of corticotrophin and β-endorphin; Science, Sep. 1981, 213, 1394-1397.

Vale, W. et al.; Chemical and biological characterization of corticotrophin releasing factor; Recent Progress in Hormone Research, 1983, 39, pp. 245-270.

J. Pharmaceutical Sciences, 1988, 77, pp. 285.

Mitchell, A.J.; The Role of corticotrophin releasing factor in depressive illness: a critical review; Neurosci. Biobehav. Rev., Sep. 1998, 5, pp. 635-651, Abstract, 1 page.

4-(2-BUTYLAMINO)-2,7-DIMETHYL-8-(2-METHYL-6-METHOXYPYRID-3-YL) PYRAZOLO-[1,5-A]-1,3,5-TRIAZINE, ITS ENANTIOMERS AND PHARMACEUTICALLY ACCEPTABLE SALTS AS CORTICOTROPIN RELEASING FACTOR RECEPTOR LIGANDS

CROSS-REFERENCE TO RELATED APPLICATIONS

This application is a divisional of U.S. application Ser. No. 10/358,652, filed Feb. 5, 2003, now U.S. Pat. No. 7,157,578, which is a continuation of U.S. application Ser. No. 10/092,312, filed Mar. 6, 2002, now abandoned, which claims the benefit of U.S. Application No. 60/275,403, filed Mar. 13, 2001, the contents all of which are incorporated herein by reference.

FIELD OF THE INVENTION

This invention relates to a treatment of psychiatric disorders and neurological diseases including major depression, anxiety-related disorders, post-traumatic stress disorder, supranuclear palsy and feeding disorders as well as treatment of immunological, cardiovascular or heart-related diseases and colonic hypersensitivity associated with psychopathological disturbances and stress, by administration of 4-(2-Butylamino)-2,7-dimethyl-8-(2-methyl-6-methoxypyrid-3-yl)pyrazolo-[1,5-a]-1,3,5-triazine, its enantiomer and pharmaceutically acceptable salts as a corticotropin releasing factor receptor ligand.

BACKGROUND OF THE INVENTION

Corticotropin releasing factor (herein referred to as CRF), a 41 amino acid peptide, is the primary physiological regulator of proopiomelanocortin (POMC)-derived peptide secretion from the anterior pituitary gland [J. Rivier et al., Proc. Nat. Acad Sci. (USA) 80:4851 (1983); W. Vale et al., Science 213:1394 (1981)]. In addition to its endocrine role at the pituitary gland, immunohistochemical localization of CRF has demonstrated that the hormone has a broad extrahypothalamic distribution in the central nervous system and produces a wide spectrum of autonomic, electrophysiological and behavioral effects consistent with a neurotransmitter or neuromodulator role in brain [W. Vale et al., Rec. Prog. Horm. Res. 39:245 (1983); G. F. Koob, Persp. Behav. Med. 2:39 (1985); E. B. De Souza et al., J. Neurosci. 5:3189 (1985)]. There is also evidence that CRF plays a significant role in integrating the response of the immune system to physiological, psychological, and immunological stressors [J. E. Blalock, Physiological Reviews 69:1 (1989); J. E. Morley, Life Sci. 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, Hosp. Practice 23:59 (1988)].

In affective disorder, or major depression, the concentration of CRF is significantly increased in the cerebrospinal fluid (CSF) of drug-free individuals [C. B. Nemeroff et al., Science 226:1342 (1984); C. M. Banki et al., Am. J. Psychiatry 144:873 (1987); R. D. France et al., Biol. Psychiatry 28:86 (1988); M. Arato et al., Biol Psychiatry 25:355 (1989)]. Furthermore, the density of CRF receptors is significantly decreased in the frontal cortex of suicide victims, consistent with a hypersecretion of CRF [C. B. Nemeroff et al., Arch. Gen. Psychiatry 45:577 (1988)]. In addition, there is a blunted adrenocorticotropin (ACTH) response to CRF (i.v. administered) observed in depressed patients [P. W. Gold et al., Am J. Psychiatry 141:619 (1984); F. Holsboer et al., Psychoneuroendocrinology 9:147 (1984); P. W. Gold et al., New Eng. J. Med. 314:1129 (1986)]. Preclinical studies in rats and non-human primates provide additional support for the hypothesis that hypersecretion of CRF may be involved in the symptoms seen in human depression [R. M. Sapolsky, Arch. Gen. Psychiatry 46:1047 (1989)]. There is preliminary evidence that tricyclic antidepressants can alter CRF levels and thus modulate the numbers of CRF receptors in brain [Grigoriadis et al., Neuropsychopharmacology 2:53 (1989)].

It has also been postulated that CRF has a role in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., Life Sci. 31:363 (1982); C. W. Berridge and A. J. Dunn Regul. Peptides 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn Horm. Behav. 21:393 (1987), Brain Research Reviews 15:71 (1990)].

Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF in both the conflict test [K. T. Britton et al., Psychopharmacology 86:170 (1985); K. T. Britton et al., Psychopharmacology 94:306 (1988)] and in the acoustic startle test [N. R. Swerdlow et al., Psychopharmacology 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., Psychopharmacology 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist (a-h elical CRF9-41) in a variety of behavioral paradigms have demonstrated that the CRF antagonist produces "anxiolytic-like" effects qualitatively similar to the benzodiazepines [for review see G. F. Koob and K. T. Britton, In: Corticotropin-Releasing Factor: Basic and Clinical Studies of a Neuropeptide, E. B. De Souza and C. B. Nemeroff eds., CRC Press p221 (1990)].

It has been further postulated that CRF has a role in cardiovascular or heart-related diseases as well as gastrointestinal disorders arising from stress such as hypertension, tachycardia and congestive heart failure, stroke, irritable bowel syndrome post-operative ileus and colonic hypersensitivity associated with psychopathological disturbance and stress [for reviews see E. D. DeSouza, C. B. Nemeroff, Editors; *Corticotropin-Releasing Factor: Basic and Clinical Studies of a Neuropeptide*, E. B. De Souza and C. B. Nemeroff eds., CRC Press p221 (1990) and C. Maillot, M. Million, J. Y. Wei, A. Gauthier, Y. Tache, Gastroenterology, 119, 1569-1579 (2000)].

Over-expression or under-expression of CRF has been proposed as an underlying cause for several medical disorders. Such treatable disorders include, for example and without limitation: affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia, hypertension, tachycardia and congestive heart failure, stroke, osteoporosis, premature birth, psychosocial dwarfism, stress-induced fever, ulcer, diarrhea, post-operative ileus and colonic hypersensitivity associated with psychopathological disturbance and stress [for reviews see J. R. McCarthy, S. C. Heinrichs and D. E. Grigoriadis, Cuur. Pharm. Res., 5, 289-315 (1999); P. J. Gilligan, D. W. Robertson and R. Zaczek, J. Medicinal Chem., 43, 1641-1660 (2000), G. P. Chrousos, Int. J. Obesity, 24, Suppl. 2, S50-S55 (2000); E. Webster, D. J. Torpy, I. J. Elenkov, G. P. Chrousos, Ann. N.Y. Acad. Sci., 840, 21-32 (1998); D. J. Newport and C. B. Nemeroff, Curr. Opin. Neurobiology, 10, 211-218 (2000); G. Mastorakos and I. Ilias, Ann. N.Y. Acad. Sci., 900, 95-106 (2000); M. J. Owens and C. B. Nemeroff, Expert Opin. Invest. Drugs, 8, 1849-1858 (1999); G. F. Koob, Ann. N.Y. Acad. Sci., 909, 170-185 (2000)].

The following publications each describe CRF antagonist compounds; however, none disclose the compounds provided herein: WO95/10506; WO99/51608; WO97/35539; WO99/01439; WO97/44308; WO97/35846; WO98/03510; WO99/11643; PCT/US99/18707; WO99/01454; and, WO00/01675.

SUMMARY OF THE INVENTION

In accordance with one aspect, the present invention provides a novel compound, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g. cerebral ischemia such as cerebral hippocampal ischemia); excitotoxic neuronal damage; epilepsy; cardiovascular and heart related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism; and hypoglycemia in a mammal.

The present invention provides a novel compound that binds to corticotropin releasing factor receptors, thereby altering the anxiogenic effects of CRF secretion. The compound of the present invention is useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in a mammal.

According to another aspect, the present invention provides a novel compound of Formula (I) (described below) which is useful as an antagonist of the corticotropin releasing factor. The compound of the present invention exhibits activity as a corticotropin releasing factor antagonist and appears to suppress CRF hypersecretion. The present invention also includes pharmaceutical compositions containing such a compound of Formula (I), and methods of using such a compound for the suppression of CRF hypersecretion, and/or for the treatment of anxiogenic disorders.

The use of competitive binding assays is considered particularly valuable for screening candidates for new drugs, e.g. to identify new CRF ligands or other compounds having even greater or more selective binding affinity for CRF receptors, which candidates would therefore be potentially useful as drugs. In the assay, one determines the ability of the candidate ligand to displace the labelled compound.

Therefore, another embodiment of the invention includes the use of a compound of the invention is a binding assay, wherein one or more of the compounds may be joined to a label, where the label can directly or indirectly provide a detectable signal. Various labels include radioisotopes, fluorescers, chemiluminescers, specific binding molecules, particles, e.g. magnetic particles, and the like.

Another embodiment of the invention is directed to the use of the compounds of the invention (particularly labeled compounds of this invention) as probes for the localization of receptors in cells and tissues and as standards and reagents for use in determining the receptor-binding characteristics of test compounds. Labeled compounds of the invention may be used for in vitro studies such as autoradiography of tissue sections or for in vivo methods, e.g. PET or SPECT scanning. Particularly, preferred compounds of the invention are useful as standards and reagents in determining the ability of a potential pharmaceutical to bind to the CRF1 receptor.

DETAILED DESCRIPTION OF THE INVENTION

[1] In a first embodiment, the present invention provides a compound of Formula (I):

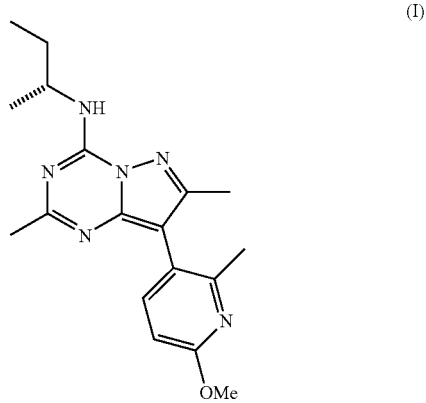

and stereoisomeric forms thereof, or mixtures of stereoisomeric forms thereof, and pharmaceutically acceptable salt or pro-drug forms thereof.

[2] In another embodiment, the present invention provides a compound of embodiment [1], isomers thereof, stereoisomeric forms thereof, mixtures of stereoisomeric forms thereof, pharmaceutically acceptable prodrugs thereof, or pharmaceutically acceptable salt forms thereof, wherein said compound is 4-((R)-2-butylamino)2,7-dimethyl-8-(2-methyl-6-methoxypyrid-3-yl)[1,5-a]-pyrazolo-1,3,5-triazine.

[3] In another embodiment, the present invention provides a compound of any one of embodiments [1] to [2], pharmaceutically acceptable prodrugs thereof, or pharmaceutically acceptable salt forms thereof, wherein said compound is substantially free of its (S) stereoisomer.

[4] In another embodiment, the present invention provides a compound of embodiment [1], wherein said compound is 4-(2-butylamino)2,7-dimethyl-8-(2-methyl-6-methoxypyrid-3-yl)[1,5-a]-pyrazolo-1,3,5-triazine.

[5] In another embodiment, the present invention provides a compound of embodiment [1], wherein said compound is 4-((R)-2-butylamino)2,7-dimethyl-8-(2-methyl-6-methoxypyrid-3-yl)[1,5-a]-pyrazolo-1,3,5-triazine.

[6] A pharmaceutical composition comprising a pharmaceutically acceptable carrier and a therapeutically effective amount of a compound of any one of embodiments [1] to [5].

[7] In another embodiment, the present invention provides a method of antagonizing a CRF receptor in a mammal, comprising administering to the mammal, a therapeutically effective amount of a compound of any one of embodiments [1] to [5].

[8] In another embodiment, the present invention provides a method of treating a disorder manifesting hypersecretion of CRF in a warm-blooded animal, comprising administering to the animal a therapeutically effective amount of a compound of any one of embodiments [1] to [5].

[9] In another embodiment, the present invention provides a method for the treatment of a disorder, the treatment of which can be effected or facilitated by antagonizing CRF, comprising administering to the mammal a therapeutically effective amount of a compound of any one of embodiments [1] to [5].

[10] In another embodiment, the present invention provides a method of antagonizing a CRF receptor in a mammal, comprising administering to the mammal, a therapeutically effective amount of a compound of any one of embodiments [1] to [5].

[11] In another embodiment, the present invention provides a method of treating anxiety or depression in mammals, comprising administering to the mammal a therapeutically effective amount of a compound of any one of embodiments [1] to [5].

[12] In another embodiment, the present invention provides a method for screening for ligands for CRF receptors, which method comprises:
a) carrying out a competitive binding assay with a CRF receptor, a compound of any one of embodiments [1] to [5] which is labelled with a detectable label, and a candidate ligand; and
b) determining the ability of said candidate ligand to displace said labelled compound.

[13] In another embodiment, the present invention provides a method for detecting CRF receptors in tissue comprising:
a) contacting a compound of any one of embodiments [1] to [5], which is labelled with a detectable label, with a tissue, under conditions that permit binding of the compound to the tissue; and
b) detecting the labelled compound bound to the tissue.

[14] In another embodiment, the present invention provides a method of inhibiting the binding of CRF to a CRF-1 receptor, comprising contacting a compound of any one of embodiments [1] to [5] with a solution comprising cells expressing the CRF1 receptor, wherein the compound is present in the solution at a concentration sufficient to inhibit the binding of CRF to the CRF-1 receptor.

[15] In another embodiment, the present invention provides an article of manufacture comprising:
a) a packaging material;
b) a compound of any one of embodiments [1] to [5]; and a label or package insert contained within said packaging material indicating that said compound is effective for treating anxiety or depression.

[16] The present invention also comprises a method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of any one of embodiments [1] to [5].

Definitions

As used herein, the term "pharmaceutically acceptable salts" refers to salts prepared from pharmaceutically acceptable non-toxic acids, including inorganic acids and organic acids. Suitable non-toxic acids include inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, n-methyl-glucamine, lysine, arginine, ornithine, choline, N,N'-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Pharmaceutically acceptable prodrugs" as used herein means any covalently bonded carriers which release the active parent drug of Formula (I) in vivo when such prodrug is administered to a mammalian subject. Prodrugs of the compounds of Formula (I) are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of formula (I), for example by hydrolysis in blood. Functional groups which may be rapidly transformed, by metabolic cleavage, in vivo form a class of groups reactive with the carboxyl group of the compounds of this invention. They include, but are not limited to such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier, 1985; Methods in Enzymology, K. Widder et al, Ed., Academic Press, 42, p. 309-396, 1985; A Textbook of Drug Design and Development, Krogsgaard-Larsen and H. Bundgaard, ed., Chapter 5; "Design and Applications of Prodrugs" p. 113-191, 1991; Advanced Drug Delivery Reviews, H. Bundgard, 8, p. 1-38, 1992; Journal of Pharmaceutical Sciences, 77, p. 285, 1988; Chem. Pharm. Bull., N. Nakeya et al, 32, p. 692, 1984; Pro-drugs as Novel Delivery Systems, T. Higuchi and V. Stella, Vol. 14 of the A.C.S. Symposium Series, and Bioreversible Carriers in Drug Design, Edward B. Roche, ed., American Pharmaceutical Association and Pergamon Press, 1987, which are incorporated herein by reference.

"Prodrugs" are considered to be any covalently bonded carriers which release the active parent drug of Formula (I) in vivo when such prodrug is administered to a mammalian subject. Prodrugs of the compounds of Formula (I) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of Formula (I), and the like.

As used herein to describe a compound, the term "substantially free of its (S) stereoisomer" means that the compound is made up of a significantly greater proportion of its (R) stereoisomer than of its optical antipode (i.e., its (S) stereoisomer). In a preferred embodiment of the invention, the term "substantially free of its (S) stereoisomer" means that the compound is made up of at least about 90% by weight of its (R) stereoisomer and about 10% by weight or less of its (S) stereoisomer.

In a more preferred embodiment of the invention, the term "substantially free of its (S) stereoisomer" means that the compound is made up of at least about 95% by weight of its (R) stereoisomer and about 5% by weight or less of its (S) stereoisomer. In an even more preferred embodiment, the term "substantially free of its (S) stereoisomer" means that the compound is made up of at least about 99% by weight of its (R) stereoisomer and about 1% or less of its (S) stereoisomer. In another preferred embodiment, the term "substantially free of its (S) stereoisomer" means that the compound is made up of nearly 100% by weight of its (R) stereoisomer. The above percentages are based on the total amount of the combined stereoisomers of the compound.

The term "therapeutically effective amount" of a compound of this invention means an amount effective to antagonize abnormal level of CRF or treat the symptoms of affective disorder, anxiety or depression in a host.

As used herein, the term "labeled" is meant that the compound is either directly or indirectly labeled with a label which provides a detectable signal, e.g. radioisotope, fluorescers, enzyme, antibodies, particles such as magnetic particles, chemiluminescer, $P^{32}$, $I^{131}$, and $At^{211}$, etc.

Syntheses

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric mixture. A 50:50 mixture of enantiomers is referred to as a racemic mixture.

The present invention includes all stereoisomeric forms of the compounds of the formula I. Centers of asymmetry that are present in the compounds of formula I can all independently of one another have S configuration or R configuration. The prefixes d and l or (+) and (−) are employed to designate the sign of rotation of plane-polarized light by the compound, with (−) or l meaning that the compound is levorotatory. A compound prefixed with (+) or d is dextrorotatory. The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula I or at the stage of an intermediate during the synthesis. The present invention also includes all tautomeric forms of the compounds of formula (I).

The compound of Formula (I) may be prepared from using the procedures outlined in Scheme 1.

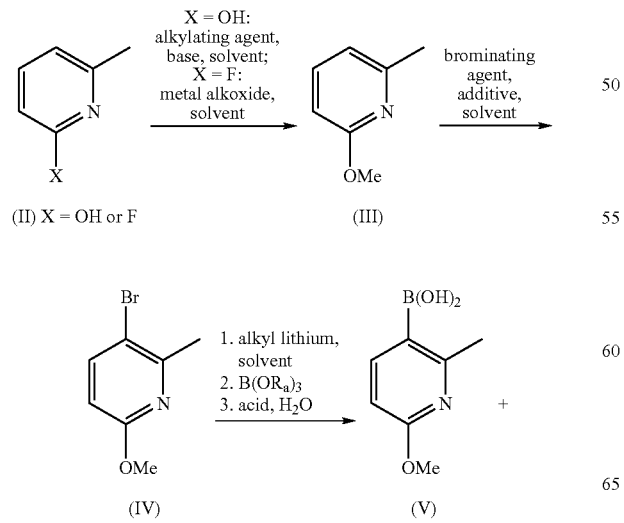

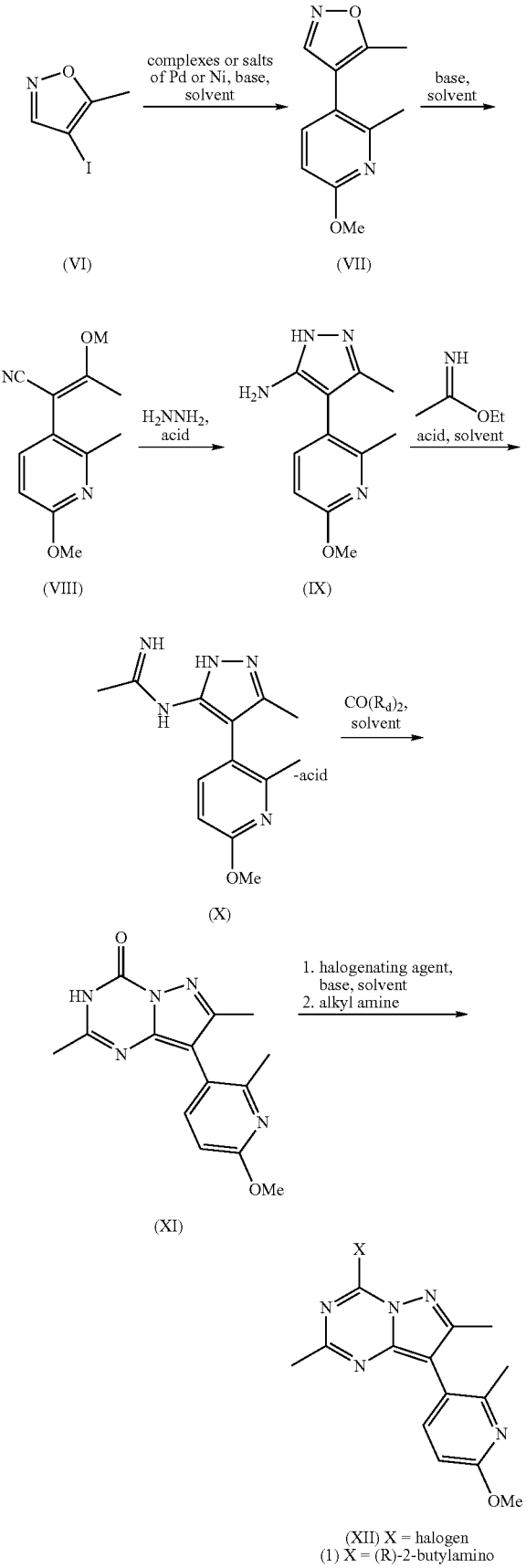

A compound of Formula (II), where X=F, may be treated with a metal alkoxide (e.g. sodium methoxide, potassium methoxide; pre-formed or generated in situ) in an inert solvent to generate an intermediate of Formula (III). Inert solvents may include, but are not limited to, alkyl alcohols (1 to 8 carbons, preferably methanol or ethanol), lower alkanenitriles (1 to 6 carbons, preferably acetonitrile), water, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 0° C. to 100° C.

Alternatively, a compound of Formula (II), where X=OH, may be treated with an alkylating agent in the presence of a base in an inert solvent to generate an intermediate of Formula (III). Alkylating agents include, but are not limited to, haloalkanes (e.g. $CH_3I$), dialkyl sulfates (e.g. $Me_2SO_4$) or alkyl trifluoro-sulfonates (e.g. $CH_3O_3SCF_3$).

Bases may include, but are not limited to, alkali metals, alkali metal hydrides (preferably sodium hydride), alkali metal alkoxides (1 to 6 carbons)(preferably sodium methoxide or sodium ethoxide), alkaline earth metal hydrides, alkali metal carbonates, alkaline metal carbonates, transition metal carbonates (e.g. silver carbonate), alkali metal dialkylamides (preferably lithium di-isopropylamide), alkali metal bicarbonates, alkali metal hydroxides, alkali metal bis(trialkylsilyl)amides (preferably sodium bis(trimethylsilyl)amide), trialkyl amines (preferably N,N-di-isopropyl-N-ethyl amine) or aromatic amines (preferably pyridine).

Inert solvents may include, but are not limited to, halocarbons (1 to 8 carbons, 1 to 8 halogens), lower alkanenitriles (1 to 6 carbons, preferably acetonitrile), water, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 50° C. to 150° C.

A compound of Formula (III) may be transformed to a compound of Formula (IV) by reaction with a brominating agent in the presence or absence of an additive in an inert solvent. Brominating agents include, but are not limited to, N-bromosuccinimide-2,2'-azobisisobutyro-nitrile (AIBN), N-bromophthalimide-2,2'-azobisiso-butyronitrile (AIBN)), bromine. Additives include, but are not limited to, alkali metal phosphates (e.g. $K_3PO_4$, $Na_3PO_4$), alkali metal hydrogen phosphates (e.g. $Na_2HPO_4$, $K_2HPO_4$), alkali metal dihydrogen phosphates (e.g. $NaH_2PO_4$, $KH_2PO_4$). Inert solvents include, but are not limited to, halocarbons (1 to 6 carbons, 1 to 6 halogens (preferably chlorine), water, N,N-dialkylformamides (preferably dimethylformamide), N,N-dialkylacetamides (preferably dimethylacetamide), cyclic amides (preferably N-methylpyrrolidin-2-one). Reaction temperatures range from 0° C. to 200° C. (preferably 20° C. to 120° C.).

A compound of Formula (IV) may be converted to a compound of Formula (V) by sequential reactions with (1) an alkyl lithium in an inert solvent at temperatures ranging from −100° C. to 50° C.; (2) a compound of the Formula $B(OR^a)_3$ (where $R^a$ is branched or straight chain alkyl of 1 to 20 carbons) at temperatures ranging from −100° C. to 50° C. and (3) an acid in the presence or absence of water at temperatures ranging from −100° C. to 100° C. Alkyl lithiums may be branched or straight chain compounds containing 1 to 20 carbons. Inert solvents include, but are not limited to, dialkyl ethers (preferably diethyl ether), cyclic ethers (preferably tetrahydrofuran or 1,4-dioxane), or aromatic hydrocarbons (preferably benzene or toluene).

Acids may include, but are not limited to, alkanoic acids of 2 to 10 carbons (preferably acetic acid), haloalkanoic acids (2-10 carbons, 1-10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid.

A compound of Formula (VII) may be produced by reaction of a compound of Formula (V) with a compound of Formula (VI) in the presence of a complex or salt of palladium or nickel, a base and an inert solvent. Complexes of palladium or nickel include, but are not limited to, phosphine complexes such as $Pd(PPh_3)_4$, $PdCl_2(PPh_3)_2$, $NiCl_2(PPh_3)_2$, or [1,1-bis(diphenylphosphino)ferrocene]-dichloropalladium. Bases may include, but are not limited to, alkali metals, alkali metal hydrides (preferably sodium hydride), alkali metal alkoxides (1 to 6 carbons)(preferably sodium methoxide or sodium ethoxide), alkali metal carbonates, alkaline metal carbonates (e.g. barium carbonate), transition metal carbonates (e.g. silver carbonate) or trialkyl amines (e.g. triethyl amine). Inert solvents may include, but are not limited to, dialkyl ethers (preferably diethyl ether), cyclic ethers (preferably tetrahydrofuran or 1,4-dioxane), or aromatic hydrocarbons (preferably benzene or toluene). Preferred reaction temperatures range from −100° C. to 100° C.

An intermediate of Formula (VII) may be reacted with a base in the presence of an inert solvent to afford a compound of Formula (VIII), where M is an alkali metal cation (e.g. sodium or potassium). Bases may include, but are not limited to, alkali metal hydroxides (e.g. NaOH or KOH), alkali metal alkoxides (1 to 6 carbons) (preferably sodium methoxide or sodium ethoxide) or alkaline earth metal hydroxides. Inert solvents may include, but are not limited to, alkyl alcohols (1 to 6 carbons), lower alkanenitriles (1 to 6 carbons, preferably acetonitrile), water, cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide). Preferred reaction temperatures range from 0° C. to 150° C.

Compounds of Formula (VIII) may be treated with hydrazine-hydrate in the presence of an acid and an inert solvent at temperatures ranging from 0° C. to 200° C., preferably 70° C. to 150° C., to produce compounds of Formula (IX). Acids may include, but are not limited to, alkanoic acids of 2 to 10 carbons (preferably acetic acid), haloalkanoic acids (2-10 carbons, 1-10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid.

Inert solvents may include, but are not limited to, water, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene).

A compound of Formula (IX) may be reacted with compounds of Formula $H_3C(C=NH)OR^c$ (where $R^c$ is alkyl (1-6 carbons)) in the presence or absence of an acid in the presence of an inert solvent at temperatures ranging from 0° C. to 200° C. to produce a compound of Formula (X). Acids may include, but are not limited to alkanoic acids of 2 to 10 carbons (preferably acetic acid), haloalkanoic acids (2-10 carbons, 1-10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used.

Inert solvents may include, but are not limited to, water, alkanenitriles (1 to 6 carbons, preferably acetonitrile), halocarbons of 1 to 6 carbons and 1 to 6 halogens (preferably dichloroethane or chloroform), alkyl alcohols of 1 to 10 carbons (preferably ethanol), dialkyl ethers (4 to 12 carbons, preferably diethyl ether or di-isopropylether) or cyclic ethers such as dioxan or tetrahydrofuran. Preferred temperatures range from 0° C. to 100° C.

A compound of Formula (X) may be converted to an intermediate compound of Formula (XI) by treatment with compounds $C=O(R^d)_2$ (where $R^d$ is halogen (preferably chlorine), alkoxy (1 to 4 carbons) or alkylthio (1 to 4 carbons)) in the presence or absence of a base in an inert solvent at reaction temperatures from −50° C. to 200° C. Bases may include, but are not limited to, alkali metal hydrides (preferably sodium hydride), alkali metal alkoxides (1 to 6 carbons) (preferably sodium methoxide or sodium ethoxide), alkali metal carbonates, alkali metal hydroxides, trialkyl amines (preferably N,N-di-isopropyl-N-ethyl amine or triethylamine) or aromatic amines (preferably pyridine).

Inert solvents may include, but are not limited to, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene).

A compound of Formula (XI) may be treated with a halogenating agent in the presence or absence of a base in the presence or absence of an inert solvent at reaction temperatures ranging from −80° C. to 250° C. to give a halogenated intermediate (XII) (where X is halogen). Halogenating agents include, but are not limited to, $SOCl_2$, $POCl_3$, $PCl_3$, $PCl_5$, $POBr_3$, $PBr_3$ or $PBr_5$. Bases may include, but are not limited to, trialkyl amines (preferably N,N-di-isopropyl-N-ethyl amine or triethylamine) or aromatic amines (preferably N,N-diethylaniline).

Inert solvents may include, but are not limited to, N,N-dialkylformamides (preferably dimethylformamide), N,N-dialkylacetamides (preferably dimethylacetamide), cyclic amides (preferably N-methylpyrrolidin-2-one) or aromatic hydrocarbons (preferably benzene or toluene). Preferred reaction temperatures range from 20° C. to 200° C.

A compound of Formula (XII) may be reacted with an alkyl amine in the presence or absence of a base in the presence or absence of an inert solvent at reaction temperatures ranging from −80 ° to 250° C. to generate compounds of Formula (I). Bases may include, but are not limited to, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal carbonates, alkali metal bicarbonates, alkali metal bis(trialkylsilyl)amides (preferably sodium bis(trimethylsilyl)amide), trialkyl amines (preferably N,N-di-isopropyl-N-ethyl amine) or aromatic amines (preferably pyridine).

Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloroethane). Preferred reaction temperatures range from 0° C. to 140° C.

The compounds of the invention may be prepared as radiolabeled compounds by carrying out their synthesis using precursors comprising at least one atom that is a radioisotope. The radioisotope is preferably selected from of at least one of carbon (preferably $^{14}C$), hydrogen (preferably $^3H$), sulfur (preferably $^{35}S$), or iodine (preferably $^{125}I$). Such radiolabeled probes are conveniently synthesized by a radioisotope supplier specializing in custom synthesis of radiolabeled probe compounds. Such suppliers include Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif.

Tritium labeled probe compounds may also conveniently be prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed in the preceding paragraph using the compound of the invention as substrate. In addition, certain precursors may be subjected to tritium-halogen exchange with tritium gas, tritium gas reduction of unsaturated bonds, or reduction using sodium borotritide, as appropriate.

Receptor autoradiography (receptor mapping) may be carried out in vitro as described by Kuhar in sections 8.1.1 to 8.1.9 of Current Protocols in Pharmacology (1998) John Wiley & Sons, New York, using radiolabeled compounds of the invention.

EXAMPLES

Analytical data were recorded for the compounds described below using the following general procedures. Proton NMR spectra were recorded on a Varian VXR or Unity 300 FT-NMR instruments (300 MHz); chemical shifts were recorded in ppm (δ) from an internal tetramethysilane standard in deuterochloroform or deuterodimethylsulfoxide as specified below. Mass spectra (MS) or high resolution mass spectra (HRMS) were recorded on a Finnegan MAT 8230 spectrometer or a Hewlett Packard 5988A model spectrometer (using chemi-ionization (CI) with $NH_3$ as the carrier gas, electrospray (ESI), atmospheric pressure chemi-ionization (APCI) or gas chromatography (GC)). Melting points were recorded on a MelTemp 3.0 heating block apparatus and are uncorrected. Boiling points are uncorrected. All pH determinations during workup were made with indicator paper.

Reagents were purchased from commercial sources and, where necessary, purified prior to use according to the general procedures outlined by D. Perrin and W. L. F. Armarego, Purification of Laboratory Chemicals, 3rd ed., (New York: Pergamon Press, 1988). Chromatography was performed on silica gel using the solvent systems indicated below. For mixed solvent systems, the volume ratios are given. Otherwise, parts and percentages are by weight. Commonly used abbreviations are: DMF (N,N-dimethylformamide), EtOH (ethanol), MeOH (methanol), EtOAc (ethyl acetate), HOAc (acetic acid), DME (1,2-diethoxyethane) and THF (tetrahydrofuran).

The following examples are provided to describe the invention in further detail. These examples, which set forth the best mode presently contemplated for carrying out the invention, are intended to illustrate and not to limit the invention.

Example 1

Preparation of 2,7-dimethyl-8(2-methyl-6-methoxy-pyrid-3-yl)[1,5-a]-pyrazolo-[1,3,5]-triazin-4(3H)-one A. 2-Methoxy-6-methylpyridine Sodium (31.0 g, 1.35 mol) was added portionwise to methanol (500 mL) over 30 min with stirring in a flask equipped with a reflux cindenser. After the addition was complete, the reaction mixture was allowed to cool to ambient temperature. 2-Fluoro-6-methylpyridine (50 g, 450 mmol) was added portionwise with stirring. The reaction mixture was then heated to reflux temperature and stirred for 48 h. The mix was then cooled to ambient temperature and solvent was removed in vacuo to provide a yellow oil. The residue was taken up in water (500 mL) and three extractions with ether (200 mL) were performed. The combined organic layers were dried over $MgSO_4$, filtered and solvent was removed in vacuo from the filtrate to give a yellow liquid: $^1$H-NMR($CDCl_3$, 300 MHz): δ 7.44 (dd, 1H, J=8, 7), 6.71 (d, 1H, J=7), 6.53 (d, 1H, J=8), 3.91 (s, 3H), 2.45 (s, 3H).

B. 2-Methoxy-6-methylpyridine

A mixture of 2-hydroxy-6-methylpyridine (6.85 g, 62.8 mmol), silver carbonate (22.5 g, 81.6 mmol), iodomethane (39.1 mL, 628 mmol) and chloroform (200 mL) was stirred at ambient temperature for 40 h in the dark. The reaction mixture was filtered through celite. The collected solid was washed with ether. The combined filtrates were concentrated in vacuo to give a liquid (6.25 g), which was identical to the product from Part A.

C. 6-Methoxy-3-bromo-2-methylpyridine

A mixture of 2-methoxy-6-methylpyridine (17.0 g, 138 mmol) and a solution of disodium hydrogen phosphate (0.15M in water, 250 mL) was stirred at room temperature. Bromine (7.1 mL, 138 mmol) was added dropwise over 15 min via an addition funnel. The reaction mixture was then stirred at room temperature for 4 h. The clear colorless solution was diluted with water (500 mL) and extracted with dichloromethane (200 mL) three times. The combined organic layers were dried over $MgSO_4$, filtered and solvent was removed in vacuo from the filtrate to give a yellow liquid. Flash chromatography on silica gel (EtOAc:hexane:: 1:20) and removal of solvent from the desired combined fractions afforded a clear colorless liquid (15.4 g): $^1$H-NMR ($CDCl_3$, 300 MHz): δ 7.60(d, 1H, J=8), 6.46 (d, 1H, J=8), 3.89 (s, 3H), 2.54 (s, 3H).

D. 6-Methoxy-2-methylpyridine-3-boronic acid

A solution of 6-methoxy-3-bromo-2-methylpyridine (59.8 g, 296 mmol) in dry THF (429 mL) was cooled with stirring to ~−78° C. under a nitrogen atmosphere. A solution of n-butyl lithium (2.5 M, 130.4 mL, 326 mmol) in hexane was added dropwise over 30 min. The reaction mixture was stirred for 3 h at ~−78° C. A solution of tri-isopropyl borate (102.7 mL, 445 mmol) in dry THF (100 mL) was added dropwise over 30 min. The reaction mixture was warmed to ambient temperature with stirring over 16 h. Acetic acid (37.35 g, 622 mmol), then water (110 mL) were added to the reaction mixture with stirring. After 2 h, the layers were separated and the organic layer was concentrated in vacuo. The residue was taken up in 2-propanol (750 mL) and solvent was removed on a rotary evaporator (bath temperature ~50° C). The residue was triturated with ether. The product was collected by filtration and dried in vacuo (48.4 g): mp>200° C.; $^1$H-NMR($CD_3OH$, 300 MHz): δ 7.83 (d, 1H, J=8), 6.56 (d, 1H, J=8), 3.85 (s, 3H), 2.44 (s, 3H); GC-MS: 168 ($M^+$+H).

E. 2-Methyl-3-(5-methylisoxazol-4-yl)-6-methoxy-pyridine

A mixture of 4-iodo-5-methylisoxazole (18.2 g, 87 mmol), 6-methoxy-2-methylpyridine-3-boronic acid (14.6 g, 87 mmol), sodium bicarbonate (22.0 g, 262 mmol), water (150 mL) and DME (150 mL) was degassed three times with stirring by the application of a vacuum and then introduction of a nitrogen atmosphere. [1,1-Bis(diphenylphosphino)ferrocene]-dichloropalladium (II) (2.14 g, 2.6 mmol) was added in one portion. The reaction mixture was degassed as before. The reaction mixture was then stirred at 80° C. for 4 h, then it was cooled to ambient temperature. Three extractions with EtOAc, drying the combined organic layers over MgSO$_4$, filtration and removal of solvent in vacuo afforded an oil. Flash chromatography (EtOAc:hexane::1:9) and removal of solvent in vacuo from the desired fractions gave the product (7.15 g): $^1$H-NMR(CDCl$_3$, 300 MHz): δ 8.16 (s, 1H), 7.33 (d, 1H, J=8), 6.63 (d, 1H, J=8), 3.95 (s, 3H), 2.35 (s, 6H); APCI$^+$-MS: 205 (M$^+$+H).

F. 1-Cyano-1-(2-methyl-6-methoxypyrid-3-yl)propan-2-one, Sodium Salt

A mixture of sodium methoxide (25% w/w, 13 mL, 70 mmol), 2-methyl-3-(5-methylisoxazol-4-yl)-6-methoxypyridine (7.15 g, 35 mmol) and methanol (50 mL) was stirred at room temperature for 16 h. Solvent was removed in vacuo to give a yellow oil. Trituration with ether, filtration and drying in vacuo afforded the crude product as a white solid (9.3 g).

G. 5-Amino-4-(2-methyl-6-methoxypyrid-3-yl)-3-methylpyrazole

A mixture of 1-cyano-1-(2-methyl-6-methoxypyrid-3-yl)propan-2-one, sodium salt (9.3 g), hydrazine-hydrate (6 mL, 123.3 mmol) and glacial acetic acid (150 mL) was stirred at room temperature for 4 h. The reaction mixture was concentrated in vacuo. The residue was dissolved in 1N HCl and the resulting solution was extracted with EtOAc two times. A 1N NaOH solution was added to the aqueous layer until pH=12. The resulting semi-solution was extracted three times with ethyl acetate. The combined organic layers were dried over MgSO$_4$ and filtered. Solvent was removed in vacuo to give a viscous oil (5.8 g): $^1$-NMR (CDCl$_3$, 300 MHz): 7.37 (d, 2H, J=8), 6.62 (d, 2H, J=8), 3.95 (s, 3H), 2.36 (s, 3H), 2.08 (s, 3H); APCI$^+$-MS: 219 (M$^+$+H); 260 (M$^+$+CH$_3$CN).

H. 5-Acetamidino-4-(2-methyl-6-methoxypyrid-3-yl)-3-methylpyrazole, acetic acid salt Ethyl acetamidate hydrochloride (6.46 g, 52.2 mmol) was added quickly to a rapidly stirred mixture of potassium carbonate (6.95 g, 50.0 mol), dichloromethane (60 mL) and water (150 mL). The layers were separated and the aqueous layer was extracted with dichloromethane (2×60 mL). The combined organic layers were dried over MgSO$_4$ and filtered. Solvent was removed by simple distillation and the pot residue, a clear pale yellow liquid, was used without further purification.

Glacial acetic acid (1.0 mL, 17.4 mmol) was added to a stirred mixture of 5-amino-4-(2-methyl-6-methoxypyrid-3-yl)-3-methylpyrazole (3.8 g, 17.4 mmol), ethyl acetamidate free base and dichloromethane (100 mL). The resulting reaction mixture was stirred at room temperature for 16 h; at the end of which time, it was concentrated in vacuo. The residue was triturated with ether, the product was filtered and washed with copious amounts of ether. The white solid was dried in vacuo (5.4 g): $^1$H-NMR (CD$_3$OH, 300 MHz): 7.43 (d, 2H, J=8), 6.69 (d, 2H, J=8), 4.9 (br s, 2H), 3.93 (s, 3H), 2.31 (s, 3H), 2.24 (s, 3H), 2.13 (s, 3H), 1.88 (s, 3H); APCI$^+$-MS: 260 (M$^+$+H).

I. 2,7-dimethyl-8-(2-methyl-6-methoxypyrid-3-yl)[1,5-a]-pyrazolo-[1,3,5]-triazin-4(3H)-one Sodium pellets (3.9 g, 169 mmol) were added portionwise to ethanol (200 mL) with vigorous stirring. After all the sodium reacted, 5-acetamidino-4-(2-methyl-6-methoxypyrid-3-yl)-3-methylpyrazole, acetic acid salt (5.4 g, 16.9 mmol) and diethyl carbonate (16.4 mL, 135.3 mmol) were added. The resulting reaction mixture was heated to reflux temperature and stirred for 18 hours. The mix was cooled to room temperature and solvent was removed in vacuo. The residue was dissolved in water and a 1N HCl solution was added slowly until pH~6. The aqueous layer was extracted with EtOAc three times; the combined organic layers were dried over MgSO$_4$ and filtered. Solvent was removed in vacuo to give a solid. Trituration with ether, filtration and drying in vacuo afforded a white solid (3.9 g): $^1$H-NMR (CD$_3$OH, 300 MHz): 7.49 (d, 2H, J=8), 6.69 (d, 2H, J=8), 3.93 (s, 3H), 2.35 (s, 3H), 2.28 (s, 3H), 2.24 (s, 3H); APCI$^+$-MS: 286 (M$^+$+H).

Example 2

Preparation of 4-((R)-2-butylamino)2,7-dimethyl-8-(2-methyl-6-methoxypyrid-3-yl)[1,5-a]-pyrazolo-1,3,5-triazine A. 4-Chloro-2,7-dimethyl-8-(2-methyl-6-methoxypyrid-3-yl)[1,5-a]-pyrazolotriazine A mixture of 2,7-dimethyl-8-(2-methyl-6-methoxypyrid-3-yl)[1,5-a]-pyrazolo-1,3,5-triazin-4-one (Example 1, 3.9 g, 13.7 mmol), di-isopropyl-ethylamine (9.5 mL, 54.7 mmol), phosphorus oxychloride (5.1 mL, 54.7 mmol) and toluene (75 mL) was stirred at reflux temperature for 4 h. The volatiles were removed in vacuo. The residue was loaded on a pad of silica gel on celite and eluted with a 1:1 mixture of EtOAc and hexane. Solvent was removed in vacuo from the filtrate to give an oil.

B. 4-((R)-2-butylamino)2,7-dimethyl-8-(2-methyl-6-methoxypyrid-3-yl)[1,5-a]-pyrazolo-1,3,5-triazine A mixture of 4-chloro-2,7-dimethyl-8-(2-methyl-6-methoxypyrid-3-yl)[1,5-a]-pyrazolotriazine, (R)-2-butylamine (2.0 mL, 20.5 mmol), di-isopropyl-ethylamine (9.5 mL, 54.7 mmol) and dry THF (25 mL) was stirred at ambient temperature for 18 hours. Solvent was removed in vacuo. Column chromatography of the residue (first using EtOAc: hexane::1:2, then using EtOAc:hexane::1:4) afforded the product. Removal of solvent in vacuo gave a white solid (2.3 g): mp=118.3° C.; $^1$H-NMR (CDCl$_3$, 300 MHz): δ 7.41 (d, 1H, J=8), 6.63 (d, 1H, J=8), 6.25 (br d, 1H, J=9), 4.35-4.30 (m, 1H), 3.95 (s, 3H), 2.49 (s, 3H), 2.35 (s, 3H), 2.30 (s, 3H), 1.76-1.66 (m, 2H), 1.34 (d, 3H, J=7), 1.02 (t, 3H, J=7); $^{13}$C-NMR (CDCl$_3$, 100.52 MHz): δ 163.8, 163.0, 155.7, 153.7, 147.8, 146.6, 141.6, 118.5, 107.4, 106.6, 53.3, 48.2, 29.7, 26.1, 22.9, 20.4, 13.1, 10.3; IR (neat, KBr, cm$^{-1}$): 3380 (m), 3371 (m), 2968 (m), 2928 (m), 2872 (w), 1621 (s), 1588 (s), 1544 (s), 1489 (s), 1460 (s), 1425 (s), 1413 (s), 1364 (s), 1346 (m), 1304 (s) 1275 (s), 1247 (s), 1198 (m), 1152 (m), 1134 (m), 1112 (m), 1034 (s), 1003 (m); ESI(+)-HRMS: Calcd for $C_{18}H_{24}N_6O$: 341.2089. Found: 341.2093 (M$^+$+H). Anal. Calcd for $C_{18}H_{24}N_6O$: C, 63.51; H, 7.12; N, 24.69. Found: C, 63.67; H, 7.00; N, 24.49.

Utility

Rat CRF Receptor Binding Assay for the Evaluation of Biological Activity.

Receptor binding affinity to rat cortical receptors was assayed according to the published methods (E. B. De Souza, J. Neuroscience, 7: 88 (1987).

Curves of the inhibition of [$^{125}$I-Tyr$^0$]-o-CRF binding to cell membranes at various dilutions of test drug were analyzed by the iterative curve fitting program LIGAND [P. J. Munson and D. Rodbard, Anal. Biochem. 107:220 (1980), which provides Ki values for inhibition which are then used to assess biological activity.

Inhibition of CRF-Stimulated Adenylate Cyclase Activity

Inhibition of CRF-stimulated adenylate cyclase activity can be performed as described by G. Battaglia et al. Synapse 1:572 (1987). Briefly, assays are carried out at 37° C. for 10 min in 200 ml of buffer containing 100 mM Tris-HCl (pH 7.4 at 37° C.), 10 mM MgCl$_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range 10$^{-9}$ to 10$^{-6m}$) and 0.8 mg original wet weight tissue (approximately 40-60 mg protein). Reactions are initiated by the addition of 1 mM ATP/$^{32}$P] ATP (approximately 2-4 mCi/tube) and terminated by the addition of 100 ml of 50 mM Tris-HCL, 45 mM ATP and 2% sodium dodecyl sulfate. In order to monitor the recovery of cAMP, 1 µl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In Vivo Biological Assay

The in vivo activity of a compound of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990).

A compound may be tested in any species of rodent or small mammal.

A compound of this invention has utility in the treatment of imbalances associated with abnormal levels of corticotropin releasing factor in patients suffering from depression, affective disorders, and/or anxiety.

A compound of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. It can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, a compound of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A method of treating anxiety or depression in mammals, comprising administering to the mammal, a therapeutically effective amount of a compound of Formula (I):

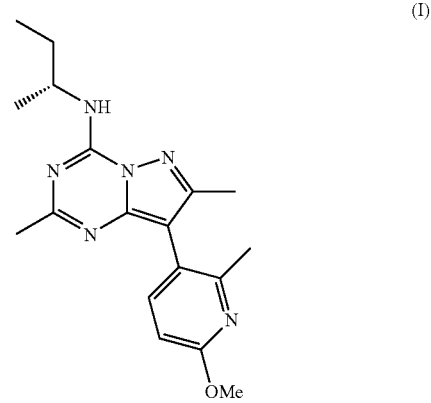

or a pharmaceutically acceptable salt form thereof.

2. The method of claim 1, wherein said compound is 4-((R)-2-butylamino)2,7-dimethyl-8-(2-methyl-6-methoxy-pyrid-3-yl)[1,5-a]-pyrazolo-1,3,5-triazine.

* * * * *